US008025058B2

(12) United States Patent
Chandran et al.

(10) Patent No.: US 8,025,058 B2
(45) Date of Patent: Sep. 27, 2011

(54) VARIABLE CPAP RESPIRATORY INTERFACE

(75) Inventors: Sanjay Chandran, Boca Raton, FL (US); Norman Hansen, Highland Beach, FL (US); Louis Javier Collazo, Pompano Beach, FL (US)

(73) Assignee: Mergenet Solutions, Inc., Coconut Creek, FL (US)

( * ) Notice: Subject to any disclaimer, the term of this patent is extended or adjusted under 35 U.S.C. 154(b) by 995 days.

(21) Appl. No.: 11/824,804

(22) Filed: Jul. 3, 2007

(65) Prior Publication Data

US 2008/0011305 A1 Jan. 17, 2008

Related U.S. Application Data

(60) Provisional application No. 60/818,687, filed on Jul. 5, 2006.

(51) Int. Cl.
*A61M 11/00* (2006.01)

(52) U.S. Cl. .............................. 128/207.11; 128/207.18

(58) Field of Classification Search ............. 128/200.24, 128/202.18, 203.22, 203.29, 204.12, 205.25, 128/206.11, 206.12, 206.18, 206.21, 206.27, 128/206.28, 207.11, 207.14
See application file for complete search history.

(56) References Cited

U.S. PATENT DOCUMENTS

| 4,018,221 A | 4/1977 | Rennie |
| 4,156,426 A | 5/1979 | Gold |
| 4,249,527 A | 2/1981 | Ko et al. |
| 4,261,355 A | 4/1981 | Glazener |
| 4,278,082 A | 7/1981 | Blackmer |
| 4,774,946 A | 10/1988 | Ackerman et al. |
| 4,782,832 A * | 11/1988 | Trimble et al. .......... 128/207.18 |
| 4,821,709 A | 4/1989 | Jensen |
| 4,821,736 A | 4/1989 | Watson |
| 4,872,832 A | 10/1989 | Alexander |
| 4,919,128 A | 4/1990 | Kopala et al. |
| 4,944,310 A | 7/1990 | Sullivan |
| 5,025,805 A * | 6/1991 | Nutter ..................... 128/207.18 |
| 5,040,532 A | 8/1991 | Alfery |
| 5,042,478 A | 8/1991 | Kopala et al. |
| 5,117,819 A | 6/1992 | Servidio et al. |
| 5,156,426 A | 10/1992 | Graves |
| 5,188,101 A | 2/1993 | Tumolo |
| 5,193,532 A | 3/1993 | Moa et al. |
| 5,220,699 A | 6/1993 | Farris |
| 5,243,971 A | 9/1993 | Sullivan et al. |
| 5,269,296 A | 12/1993 | Landis |
| 5,271,391 A | 12/1993 | Graves |
| 5,361,416 A | 11/1994 | Petrie et al. |
| 5,477,852 A | 12/1995 | Landis et al. |
| 5,538,000 A | 7/1996 | Rudolph |
| 5,682,881 A | 11/1997 | Winthrop et al. |
| 5,687,715 A | 11/1997 | Landis et al. |
| 5,687,743 A | 11/1997 | Goodwin |

(Continued)

*Primary Examiner* — Steven O Douglas
(74) *Attorney, Agent, or Firm* — Adam C. Underwood; Carey, Rodriguez, Greenberg & Paul LLP

(57) ABSTRACT

The present disclosure relates generally connectors for interconnecting a conduit of a fluid pressure device to an interface configured to deliver a fluid of the fluid pressure device to a patient. A connector includes a body portion configured for fluid connection to the conduit of the fluid pressure device; and a first branch and a second branch each extending from and fluidly connected to the body portion, wherein each branch is configured for fluid connection to the interface. A concavity is formed at an interface between each of the body portions, the first branch and the second branch.

28 Claims, 17 Drawing Sheets

U.S. PATENT DOCUMENTS

| | | |
|---|---|---|
| 5,724,965 A | 3/1998 | Handke et al. |
| 5,975,077 A | 11/1999 | Hofstetter et al. |
| 6,119,693 A | 9/2000 | Kwok et al. |
| 6,119,694 A | 9/2000 | Correa et al. |
| 6,192,886 B1 | 2/2001 | Rudolph |
| 6,418,928 B1 | 7/2002 | Bordewick et al. |
| 6,418,929 B1 | 7/2002 | Norfleet |
| 6,422,238 B1 | 7/2002 | Lithgow |
| 6,427,694 B1 | 8/2002 | Hecker et al. |
| 6,431,172 B1 | 8/2002 | Bordewick |
| 6,439,230 B1 | 8/2002 | Gunaratnam et al. |
| 6,439,234 B1 | 8/2002 | Curti et al. |
| 6,470,886 B1 | 10/2002 | Jestrabek-Hart |
| 6,489,234 B1 | 12/2002 | Itoh |
| 6,494,207 B1 | 12/2002 | Kwok |
| 6,561,191 B1 | 5/2003 | Kwok |
| 6,595,215 B2 | 7/2003 | Wood |
| 6,679,265 B2 * | 1/2004 | Strickland et al. ....... 128/207.18 |
| 6,769,432 B1 | 8/2004 | Keifer |
| 6,823,865 B2 | 11/2004 | Drew et al. |
| 6,994,089 B2 * | 2/2006 | Wood ....................... 128/207.18 |
| 2006/0124131 A1 | 6/2006 | Chandran et al. |

* cited by examiner

VARIABLE CPAP RESPIRATORY INTERFACE

CROSS REFERENCE TO RELATED APPLICATION

The present application claims priority, under 35 U.S.C. §119, to U.S. Provisional Patent Application No. 60/818,687, filed on Jul. 5, 2006, the entire content of which is incorporated herein by reference in its entirety.

BACKGROUND

1. Technical Field

The present disclosure relates generally to the field of respiratory therapy and, more particularly, to a continuous positive airway pressure (CPAP) interfaces and the like.

2. Background of Related Art

Obstructive sleep apnea syndrome (commonly referred to as obstructive sleep apnea, sleep apnea syndrome, and/or sleep apnea) is a medical condition that includes repeated, prolonged episodes of cessation of breathing during sleep. During a period of wakefulness, the muscles of the upper part of the throat passage of an individual keep the passage open, thereby permitting an adequate amount of oxygen to flow into the lungs. However, during sleep, the throat passage tends to narrow due to the relaxation of the muscles.

In those individuals having a relatively normal-sized throat passage, the narrowed throat passage remains open enough to permit the adequate amount of oxygen to flow into the lungs. However, in those individuals having a relatively smaller-sized throat passage, the narrowed throat passage prohibits the adequate amount of oxygen from flowing into the lungs. Additionally, a nasal obstruction, such as a relatively large tongue, and/or certain shapes of the palate and/or the jaw of the individual, further prohibit the adequate amount of oxygen from flowing into the lungs.

Other medical conditions can also prevent individuals, including adults and infants, from receiving the adequate amount of oxygen into the lungs. For example, an infant who is born prematurely can have lungs that are not developed to an extent necessary to receive an adequate amount of oxygen. Further, prior to, during, and/or subsequent to certain medical procedures and/or medical treatments, an individual can be unable to receive an adequate amount of oxygen. Under these circumstances, it is known to use a ventilation interface to apply a positive pressure to the throat of the individual, thereby permitting the adequate amount of oxygen to flow into the lungs.

In the known ventilation interface, oxygen and/or room air containing oxygen is delivered through the mouth and/or nose of the individual. Existing types of positive pressure applied by the known ventilation interface include continuous positive airway pressure (CPAP), in which a positive pressure is maintained in the throat passage throughout a respiratory cycle, bi-level positive airway pressure (BiPAP), in which a relatively high positive pressure is maintained during inspiration and a relatively low positive pressure is maintained during expiration, and intermittent mechanical positive pressure ventilation (IPPV) in which a positive pressure is applied when apnea is sensed (i.e., the positive airway pressure is applied intermittently or non-continuously).

Typical prior art ventilation masks may be worn in such a manner that fluid conduits thereof extend down to lie on or against a patients chest or may be worn in such a manner that the fluid conduits thereof extend over the patients head. These ventilation masks incorporate the use of various fixed dimensioned Y-connector or ventilation interfaces such as, for example, a 0° Y-connector for ventilation masks which include fluid conduits which overlie the chest, and a 60°-75° Y-connector for ventilation masks which include fluid conduits which extend over the patients head. These fixed dimensioned Y-connector or ventilation interfaces contribute to the patient's inability to adjust the mask and harness as needed or desired in order to achieve a sufficient level of comfort.

A patient's most common complaint regarding prior art ventilation masks is that they cause claustrophobia. Such masks have tubing or mask components that go directly over the eyes or mouth of the patient. Therefore, the user feels as if they are in a tunnel, which feeling is uncomfortable to the user.

It would be desirable, therefore, to provide a breathing mask that reduces the feeling of claustrophobia, improves the fit and comfort, and provides an economical and sanitary solution to problems with conventional breathing masks Accordingly, a need also exists for a ventilation interface which may have a variable angle so that the patient may alter the wearing position as needed and or desired without effecting the transmission of air therethrough.

SUMMARY

The present disclosure relates generally to respiratory devices, continuous positive airway pressure (CPAP) interfaces, ventilation interfaces, fluid connectors and the like.

According to an aspect of the present disclosure, a connector for interconnecting a conduit of a fluid pressure device to an interface configured to deliver a fluid of the fluid pressure device to a patient is provided. The connector includes a body portion configured for fluid connection to the conduit of the fluid pressure device; and a first branch and a second branch extending from and fluidly connected to the body portion, wherein each branch is configured for fluid connection to the interface. At least one concavity is formed in at least one of the body portion, the first branch and the second branch.

At least one of the first branch and the second branch may be pivotable with respect to the body portion. The connector may be fabricated from a resilient, elastomeric material.

Each of the body portion, the first branch and the second branch may have a substantially circular transverse cross-sectional profile. Each of the body portion, the first branch and the second branch may define a longitudinal axis.

The longitudinal axis of each of the first branch and the second branch may be angled with respect to at least one of each other and with respect to the longitudinal axis of the body portion. An angle between a longitudinal axis of each of the first branch and the second branch may be variable.

Each of the body portion, the first branch and the second branch may have a respective wall thickness. Each concavity may have a wall thickness which may be less that the wall thickness of each of the body portion, the first branch and the second branch. At least one concavity may be a thin-walled region.

The connector may further include a swivel joint connected to the body portion, and a stem extending from the swivel joint.

According to another aspect of the present disclosure, a respiratory device configured for delivering fluid to a patient from a fluid source is provided. The respiratory device comprises a connector for connection to a fluid conduit extending of the fluid source. The connector includes a body portion configured for fluid connection to the fluid conduit; and a first branch and a second branch each extending from and fluidly connected to the body portion; wherein at least one concavity is formed in at least one of the body portion, the first branch and the second branch. The respiratory device includes a fluid delivery element extending from each of the first branch and the second branch of the connector. The respiratory system further includes a ventilation interface fluidly connected to each of fluid delivery element. The ventilation interface includes a cannula body defining a cavity; at least one vent formed in the cannula body and defining a passage into the cavity of the cannula body; and at least one engaging element supported on the cannula body and being in fluid communication with the cavity of the cannula body. Each fluid delivery element is pivotally connected to the cannula body.

The ventilation interface may include a coupling element configured to pivotally interconnect each fluid delivery element to the cannula body. Each coupling element of the ventilation interface may be an elbow joint. Each coupling element of the ventilation interface may be pivotally connected to the cannula body and each fluid delivery element may be pivotally connected to a respective coupling element.

Each engaging element of the ventilation interface may be a nasal pillow. Each nasal pillow may be tethered to one another.

At least one of the first branch and the second branch of the connector may be pivotable with respect to the body portion thereof. The connector may be fabricated from a resilient, elastomeric material.

Each of the body portion, the first branch and the second branch of the connector may have a substantially circular transverse cross-sectional profile. Each of the body portion, the first branch and the second branch of the connector may define a longitudinal axis. The longitudinal axis of each of the first branch and the second branch of the connector may be angled with respect to at least one of each other and with respect to the longitudinal axis of the body portion. An angle between the longitudinal axes of each of the first branch and the second branch of the connector may be variable.

Each of the body portion, the first branch and the second branch of the connector may have a respective wall thickness. Each concavity may have a wall thickness which may be less that the wall thickness of each of the body portion the first branch and the second branch. At least one concavity of the connector may be a thin-walled region.

The connector may further include a swivel joint connected to the body portion, and a stem extending from the swivel joint.

BRIEF DESCRIPTION OF THE DRAWINGS

By way of example only, preferred embodiments of the disclosure will be described with reference to the accompanying drawings, in which.

DETAILED DESCRIPTION OF EMBODIMENTS

Figure 1:
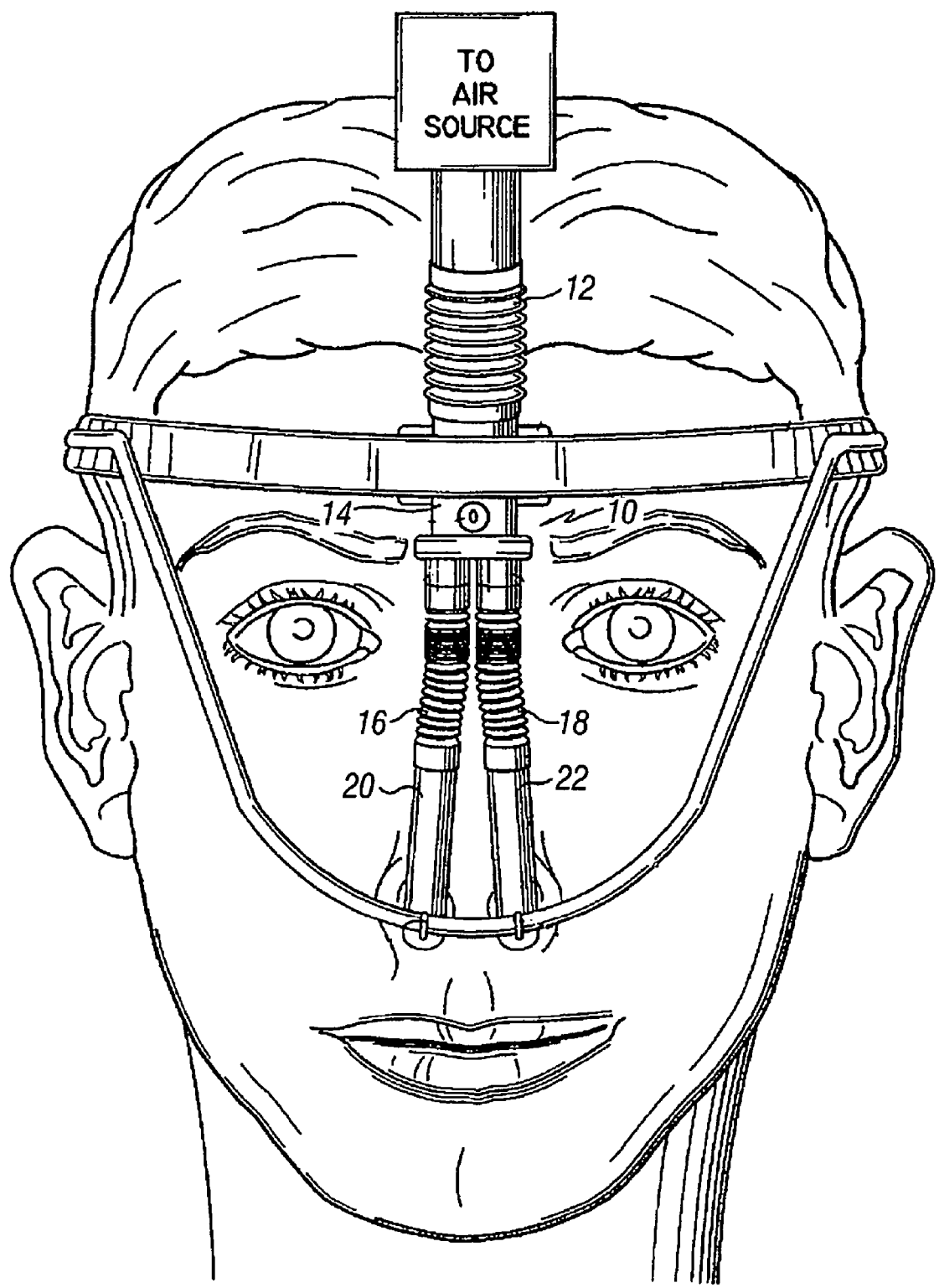
FIG. 1 is a front elevational view of a prior art positive airway pressure device.

Reference is now made specifically to the drawings in which identical or similar elements are designated by the same reference numerals throughout. In the drawings and in the description which follows, the term "proximal", as is traditional will refer to the end of the device or apparatus which is closest to the patient, while the term "distal" will refer to the end of the device or apparatus which is furthest from the patient.

With reference to FIG. 1, a front elevational view of a prior art positive airway pressure device is shown and generally designated as 10. Device 10 generally consists of a primary tube 12, a plenum chamber 14, and a pair of tubes 16, 18 connected to fluid delivery elements 20, 22, respectively. As shown, plenum chamber 14 is positioned adjacent the forehead of the user. Plenum chamber 14 is typically made of a substantially rigid material, such as rigid plastic or metal. As such, the shape and configuration of plenum chamber 14 is typically fixed.

Figure 2:
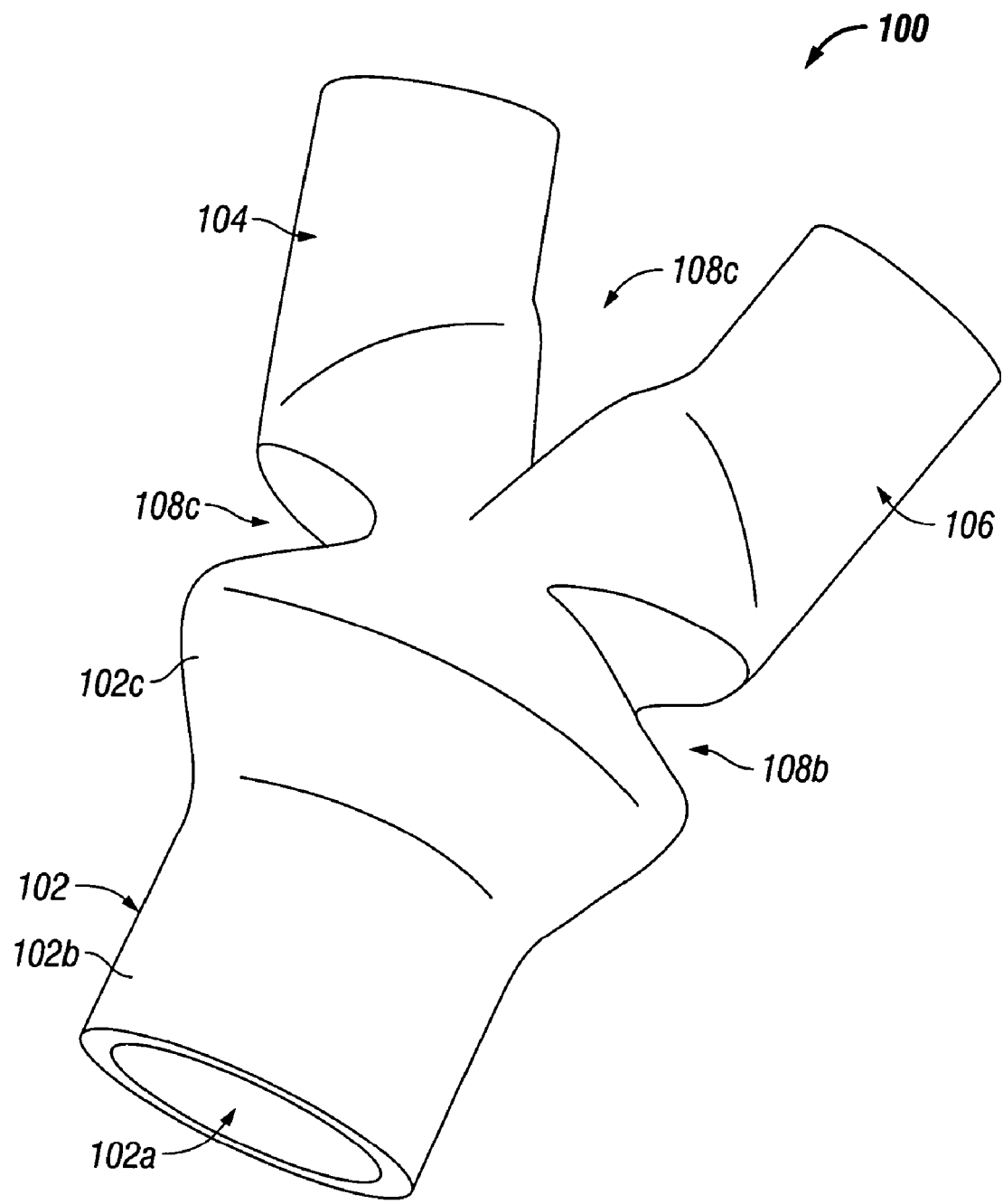
FIG. 2 is a perspective view of a Y-connector for a continuous positive airway pressure (CPAP) interface according to an embodiment of the resent disclosure.
Figure 3:
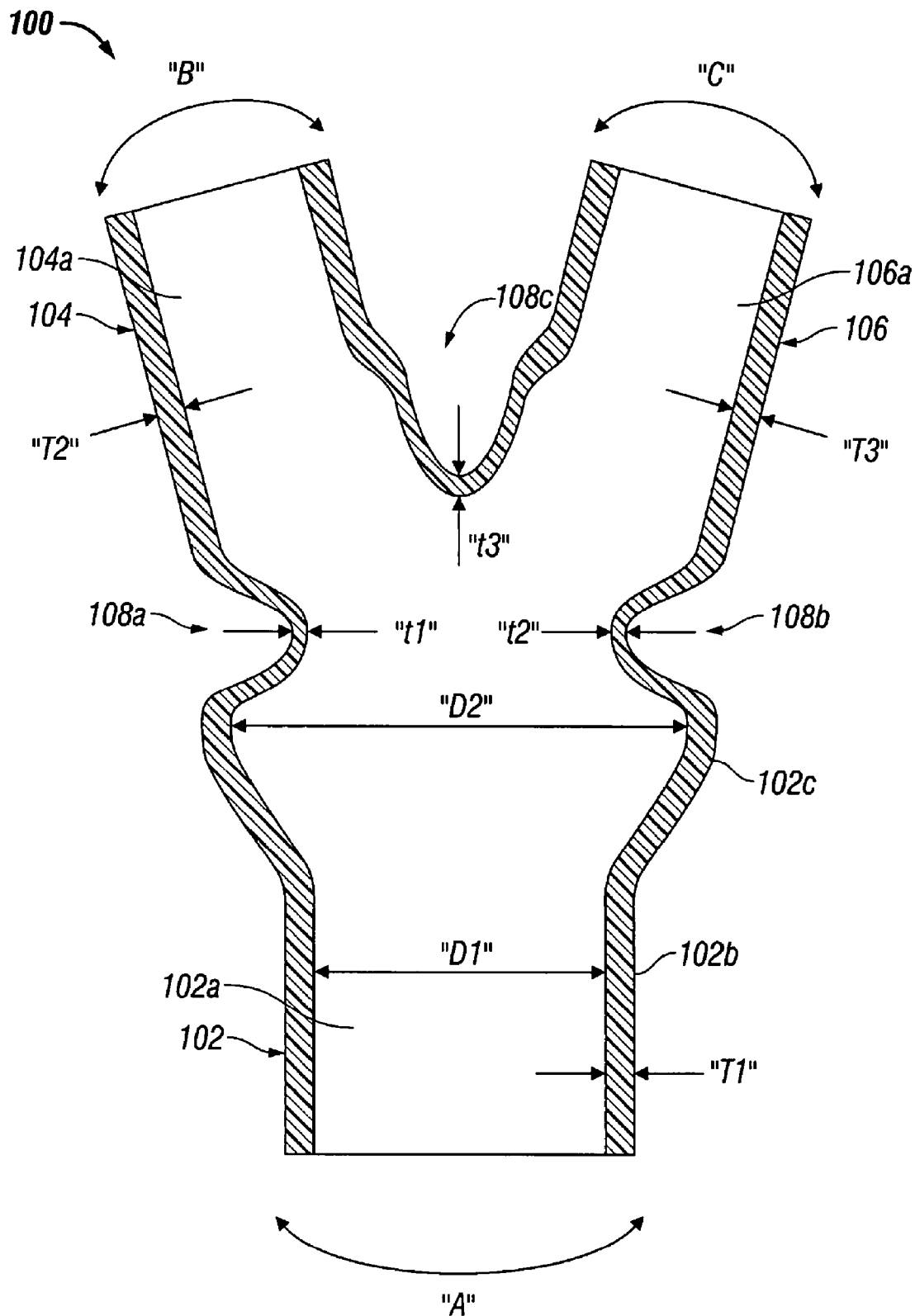
FIG. 3 is a longitudinal cross-sectional view of the Y-connector of FIG. 2.

Turning now to FIGS. 2 and 3, a connector for a continuous positive airway pressure (CPAP) interface or plenum is shown and generally designated as 100. Connector 100 has a substantially "Y-shape" and includes a trunk or body portion 102 configured and adapted for connection to a primary tube 12 (see FIG. 1) and a pair of branches, legs or arms 104, 106, extending from body portion 102 and each being configured and adapted for connection to a respective delivery (element 20, 22 (see FIG. 1). Body portion 102 defines a lumen 102*a* therethrough having a divided path 104*a*, 106*a*, which extends through each branch 104, 106, respectively.

As seen in FIGS. 2 and 3, Y-connector 100 includes concavity or groove 108a, 108b and 108c, respectively formed at an intersection between body portion 102 and first branch 104, between body portion 102 and second branch 106, and between first branch 104 and second branch 106. Concavities 108a-108c enable body portion 102 to pivot and/or move independently with respect to first and second branches 104, 106 (as indicated by double-headed arrow "A"), enable first branch 104 to pivot or move independently with respect to body portion 102 and second leg 106 (as indicated by double-headed arrow "B"), and enable second branch 106 to pivot or move independently with respect to body portion 102 and first leg 104 (as indicated by double-headed arrow "C").

As seen in FIG. 3, body portion 102, first branch 104 and second branch 106 have a substantially uniform wall thickness "T1-T3", respectively. Each of concavities 108a-108c has a wall thickness "t1-t3", respectively, which is relatively less than the wall thicknesses "T1-T3" of body portion 102, first branch 104 and second branch 106, respectively. As such, the pivotability and/or movability of body portion 102, first branch 104 and second branch 106 with respect to one another is enhanced.

With continued reference to FIGS. 2 and 3, each of body portion 102, first branch 104 and second branch 106 has a substantially cylindrical shape having a substantially circular transverse cross-sectional profile. While each of body portion 102, first branch 104 and second branch 106 is shown and described as having a circular cross-sectional profile, it is envisioned and contemplated that each of body portion 102, first branch 104 and second branch 106 may have any shape, configuration and or cross-sectional profile, including and not limited to rectangular, ovular, triangular and the like.

As seen in FIGS. 2 and 3, body portion 102 has a first section 102b having a fixed or uniform diameter "D1" and a second section 102c, adjacent each of first and second branches 104, 106, having an enlarged or radially expanding diameter "D2".

Y-connector 100 is preferably fabricated from a resilient, elastic material which can be molded and/or formed into a desired shape and which retains its shape and still provides a degree of flexibility, resiliency and/or elasticity, such as, for example, silicone, rubber, polyethylene, polypropylene and the like.

Figure 4:
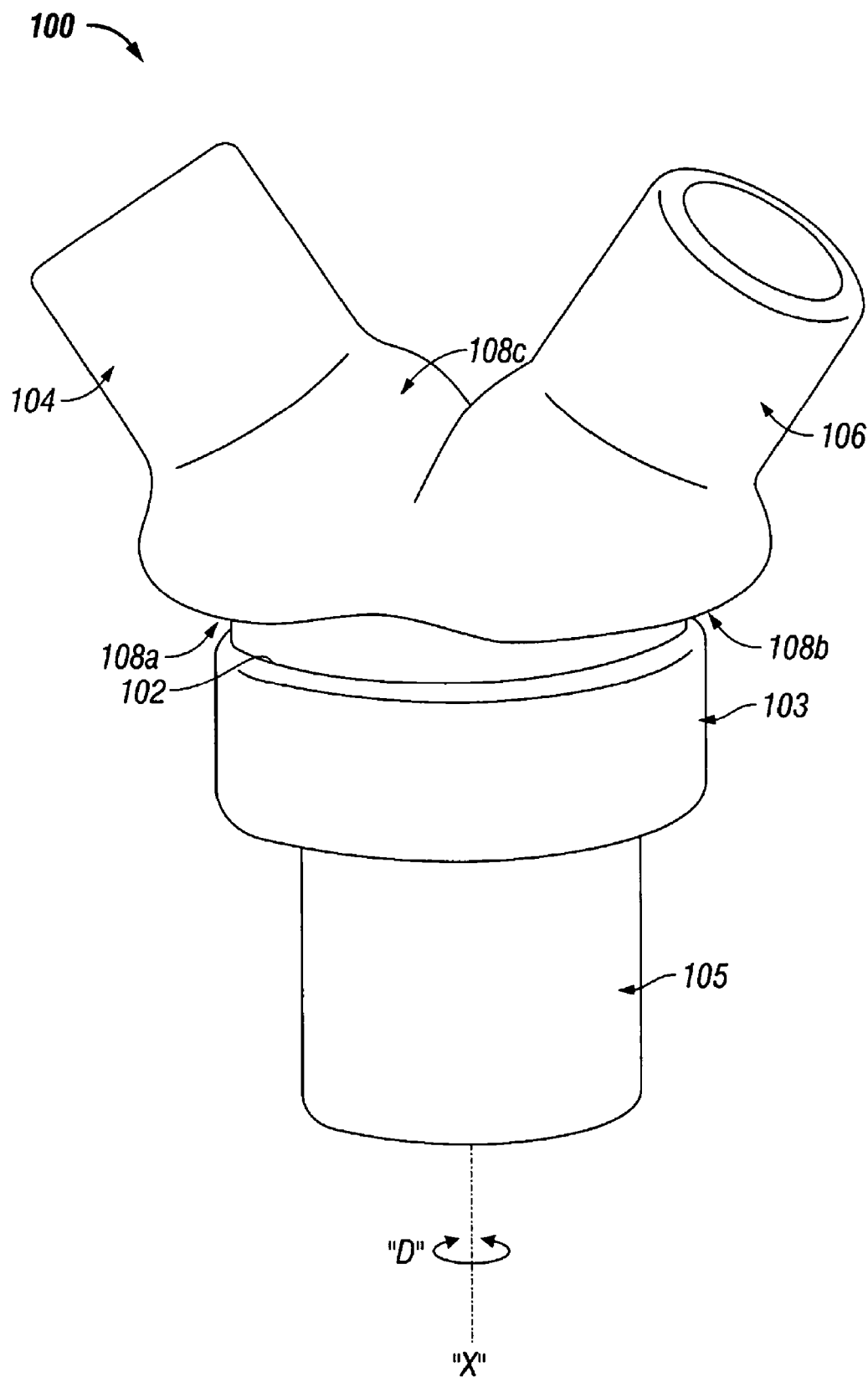
FIG. 4 is a perspective view of a variation of the Y-connector of FIGS. 2 and 3.
Figure 5:
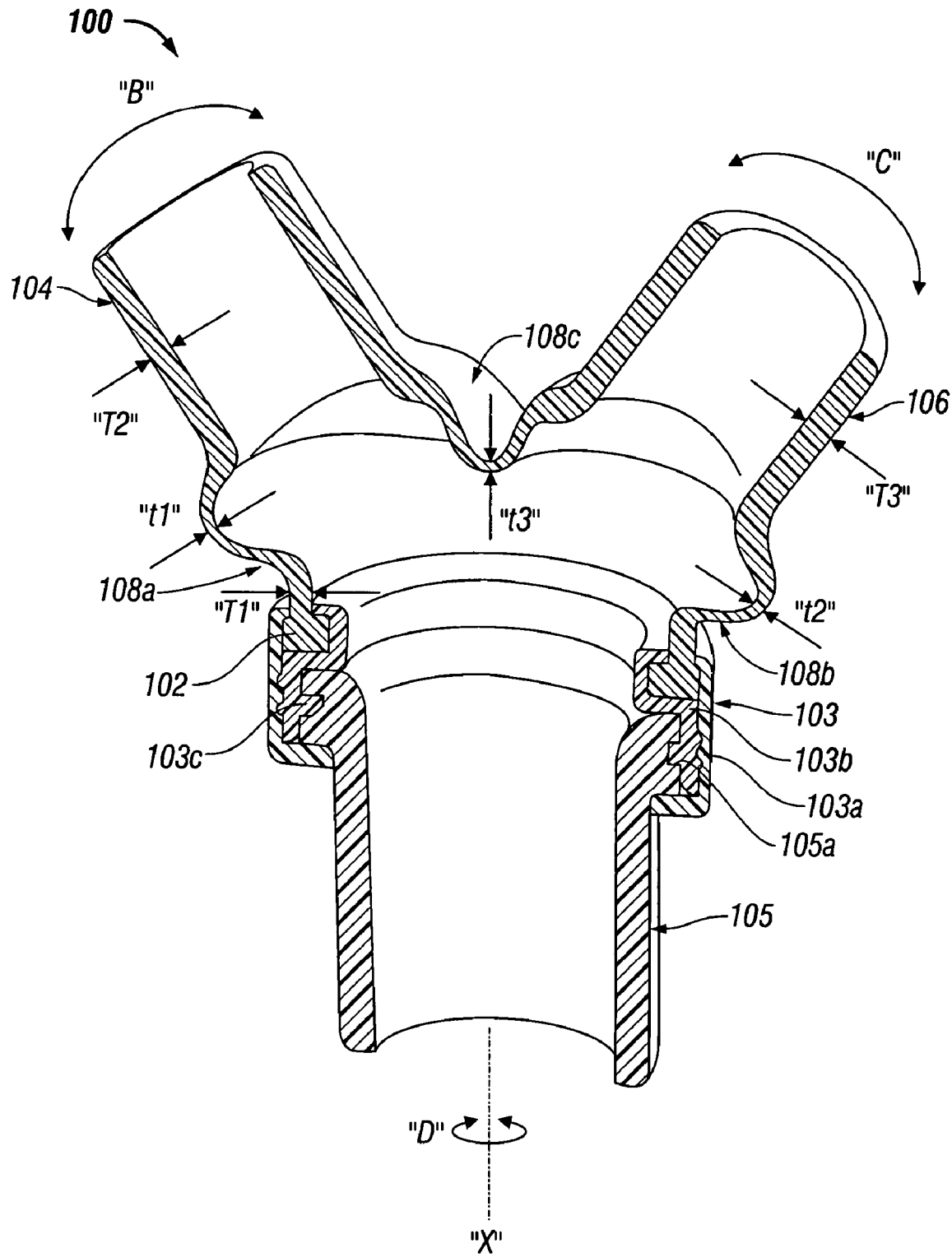
FIG. 5 is a longitudinal cross-sectional view of the Y-connector of FIG. 4.

Turning now to FIGS. 4 and 5, a variation of Y-connector 100 is generally shown as Y-connector 100'. As seen in FIGS. 4 and 5, body portion 102 of Y-connector 100' is secured within a swivel joint 103. Y-connector 100' further includes a stalk or stem 105 extending from swivel joint 103. Stem 105 is in fluid communication with body portion 102 and with first and second branches 104, 106, respectively.

Stem 105 defines a central axis "X" about which swivel joint 103 allows body portion 102 and with first and second branches 104, 106 to rotate, as indicated by double-headed arrow "D".

Swivel joint 103 includes an outer retaining ring 103a and an inner retaining ring 130b, wherein outer retaining ring 103a and inner retaining ring 103b are configured for fixed connection to one another and are configured for securing body portion 102 therebetween. Stem 105 defines an annular race 105a formed in an outer surface thereof for rotatable and slidable connection with an annular wall 103c extending or projecting from inner retaining ring 103b.

As seen in FIG. 5, body portion 102, first branch 104 and second branch 106 have a substantially uniform wall thickness "T1-T3", respectively. Each of concavities 108a-108c has a wall thickness "t1-t3", respectively, which is relatively less than the wall thicknesses "T1-T3" of body portion 102, first branch 104 and second branch 106, respectively. As such, the pivotability and/or movability of body portion 102, first branch 104 and second branch 106 with respect to one another is enhanced.

Figure 6:
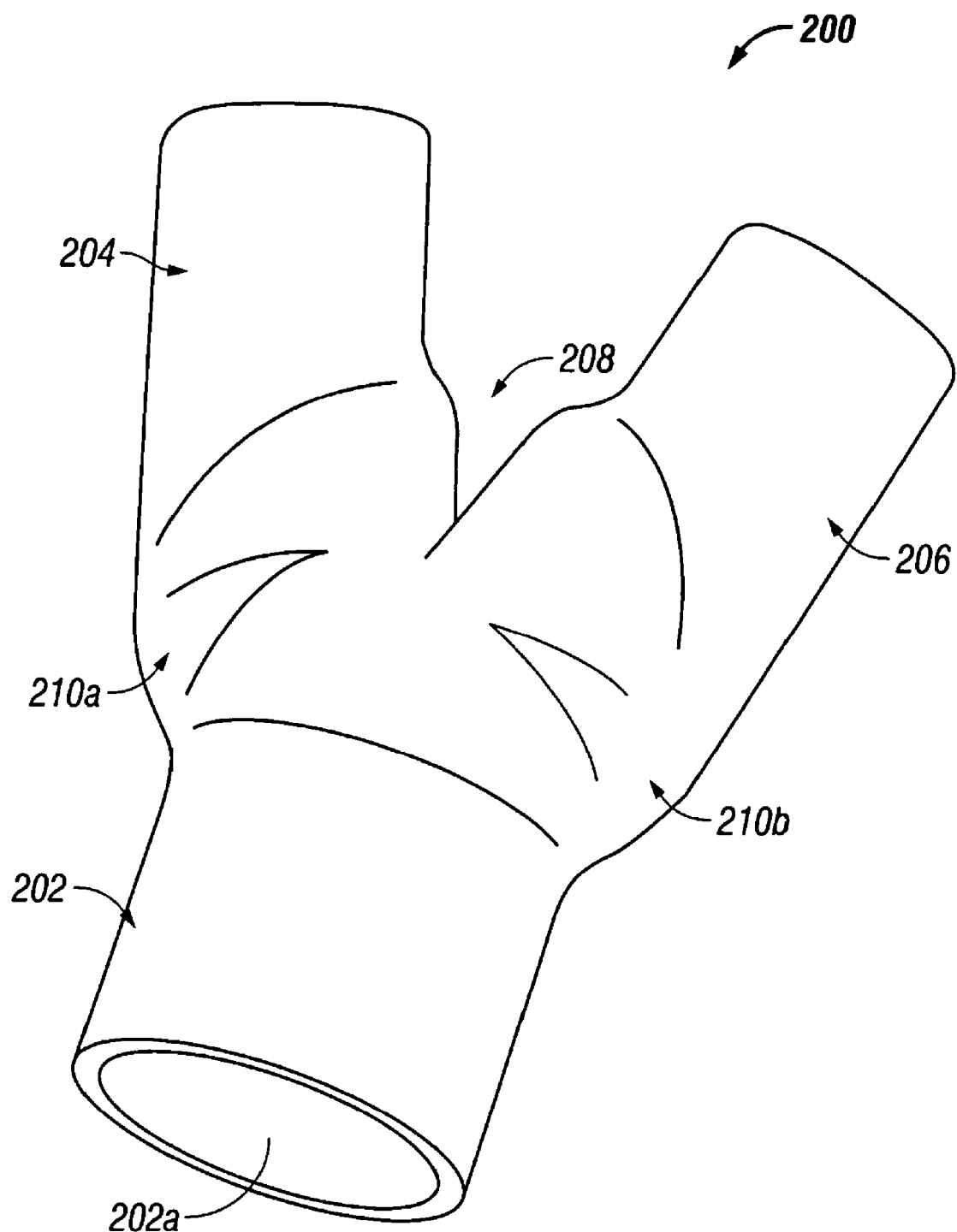
FIG. 6 is a perspective view of a Y-connector according to another embodiment of the present disclosure.
Figure 7:
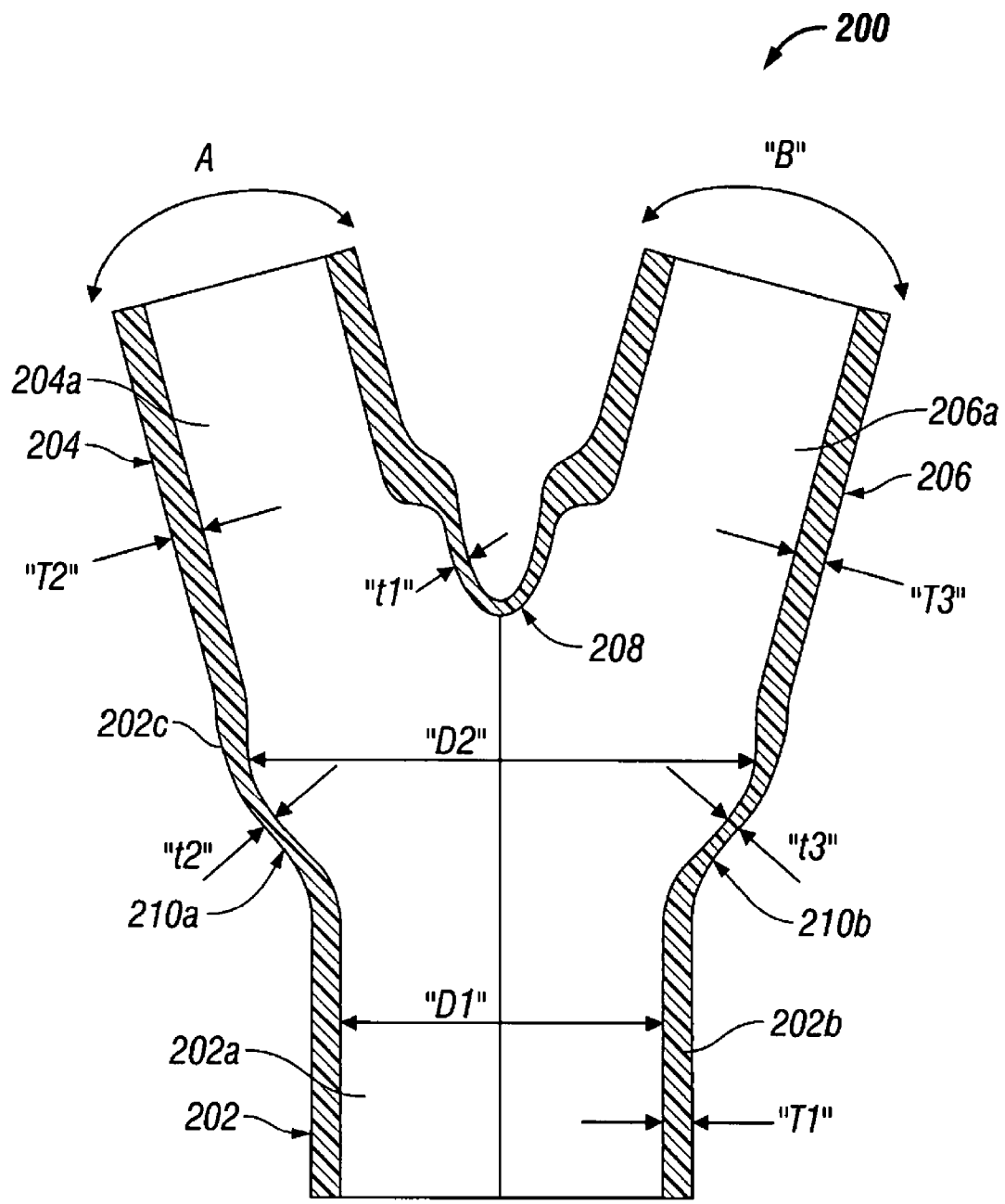
FIG. 7 is a longitudinal cross-sectional view of the Y-connector of FIG. 6.

Turning now to FIGS. 6 and 7, a connector for a continuous positive airway pressure (CPAP) interface or plenum, in accordance with another embodiment of the present disclosure, is generally designated as 200. Connector 200 has a substantially "Y-shape" and includes a trunk or body portion 202 configured and adapted for connection to a primary tube 12 (see FIG. 1) and a pair of branches, legs or aims 204, 206, extending from body portion 202 and each being configured and adapted for connection to a respective delivery element 20, 22 (see FIG. 1). Body portion 202 defines a lumen 202a therethrough having a divided path 204a, 206a, which extends through each branch 204, 206, respectively.

As seen in FIGS. 6 and 7, Y-connector 200 includes concavity or groove 208 formed at an intersection between first branch 204 and second branch 206. Concavity 208 enables first branch 204 and second branch 206 to pivot or move independently with respect to one another (as indicated by double-headed arrows "A and B").

As seen in FIG. 7, body portion 202, first branch 204 and second branch 206 have a substantially uniform wall thickness "T1-T3", respectively. Concavity 208 has a wall thickness "t1" which is relatively less than the wall thicknesses "T1-T3" of body portion 102, first branch 104 and second branch 106, respectively. Additionally, CPAP interface 200 includes a first thin-walled region 210a interposed between body portion 202 and first branch 204, and a second thin-walled region 210b interposed between body portion 202 and second branch 206. First thin-walled region 210a has a wall thickness "t2" which is relatively less than the wall thicknesses "T1-T3" of body portion 102. Second thin-walled region 210b has a wall thickness "t3" which is relatively less than the wall thicknesses "T1-T3" of body portion 102. Thin walls "t1-t3" of concavity 208, first thin-walled region 210a and second thin-walled section 210b, respectively, enhance the pivotability and/or movability of body portion 202, first branch 204 and second branch 206 with respect to one another.

With continued reference to FIGS. 6 and 7, each of body portion 202, first branch 204 and second branch 206 has a substantially cylindrical shape having a substantially circular transverse cross-sectional profile. While each of body portion 202, first branch 204 and second branch 206 is shown and described as having a circular cross-sectional profile, it is envisioned and contemplated that each of body portion 202, first branch 204 and second branch 206 may have any shape, configuration and or cross-sectional profile, including and not limited to rectangular, ovular, triangular and the like.

As seen in FIGS. 6 and 7, body portion 202 has a first section 202b having a fixed or uniform diameter "D1" and a second section 202c, adjacent each of first and second branches 204, 206, having an enlarged or radially expanding diameter "D2".

Y-connector 200 is preferably fabricated from a resilient, elastic material which can be molded and/or formed into a desired shape and which retains its shape and still provides a degree of flexibility, resiliency and/or elasticity, such as, for example, silicone, rubber, polyethylene, polypropylene and the like.

In accordance with the present disclosure, each of Y-connectors 100, 100' and 200, enables the angle between first and second branches to be easily varied without affecting the rate of fluid or air flow therethrough. As such, a patient wearing a CPAP device is capable of altering and/or varying the wearing position of the CPAP device from the chest to over-head in order to accommodate different sleep positions and the Y-connectors 100, 100' or 200 will adapt accordingly.

It is envisioned that each of the concavities and/or thin-walled regions disclosed herein for Y-connectors 100, 100' and 200 may include pleats and/or bellows to further enhance the flexing and/or pivoting action of the body portion, the first branch and the second branch with respect to one another. It is further envisioned that Y-connectors 100, 100' and 200 may include a plurality of rigid elements defining the pivot points between the body portion, the first branch and the second branch which may accommodate an air path therethrough and which may enable angles between the body portion, the first branch and the second branch to be varied.

Turning now to FIGS. 8-17, a ventilation interface in accordance with an embodiment of the present disclosure is generally designated as 300. The ventilation interface 300 provides an interface for connecting a ventilation device which provides positive airway pressure (either continuous, bilevel, or intermittent) with the patient's airways.

As seen in FIGS. 8-17, ventilation interface 300 includes my one of Y-connector 100, 100' and 200 (see FIGS. 2-7) having a first end or body portion 102, 202 adapted to receive a primary tube 12 (see FIG. 1) from an air source and a pair of branches 104, 204 and 106, 206 each connected to a respective fluid delivery element or supply tube 20, 22 (see FIG. 1). Ventilation interface 300 further includes a cannula body 302 defining a cavity 302a therewithin, and a pair of nozzles or nasal pillows 304, 306 removably connected to cannula body 302 along a same side thereof.

Figure 8:
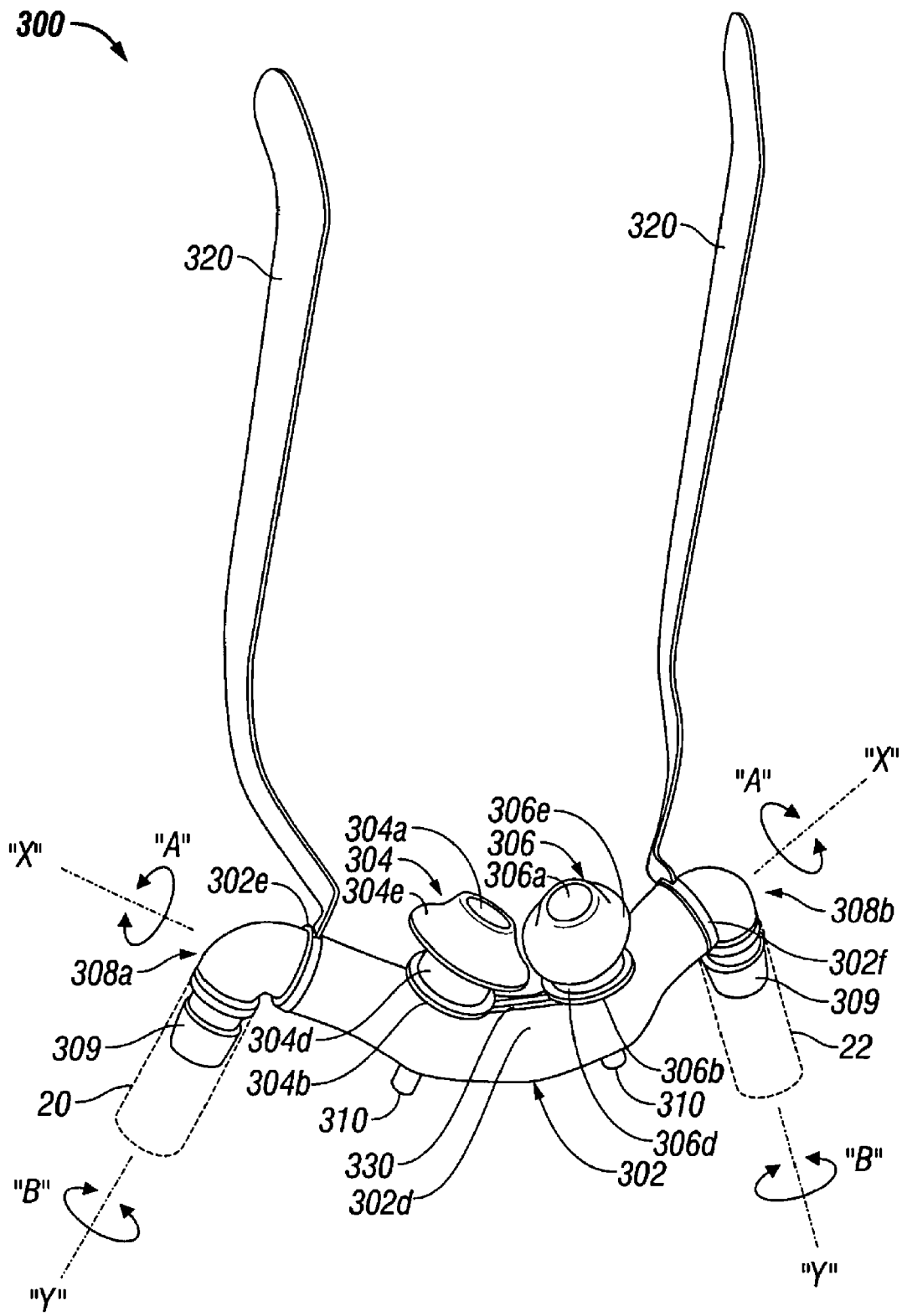
FIG. 8 is a perspective view of a ventilation interface in accordance with an embodiment of the present disclosure.
Figure 9:
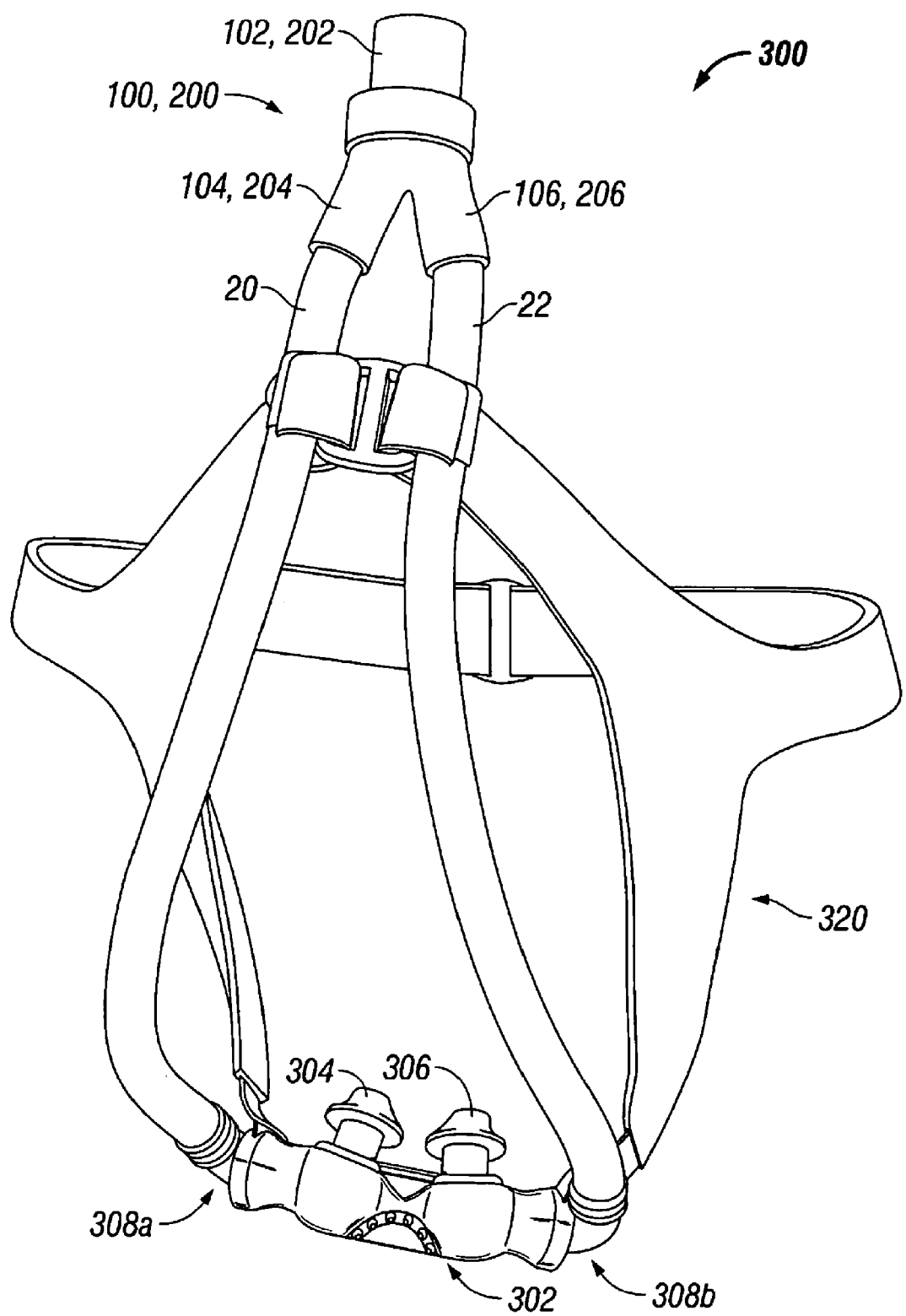
FIG. 9 is a further perspective view of the ventilation interface of FIG. 8.
Figure 10:
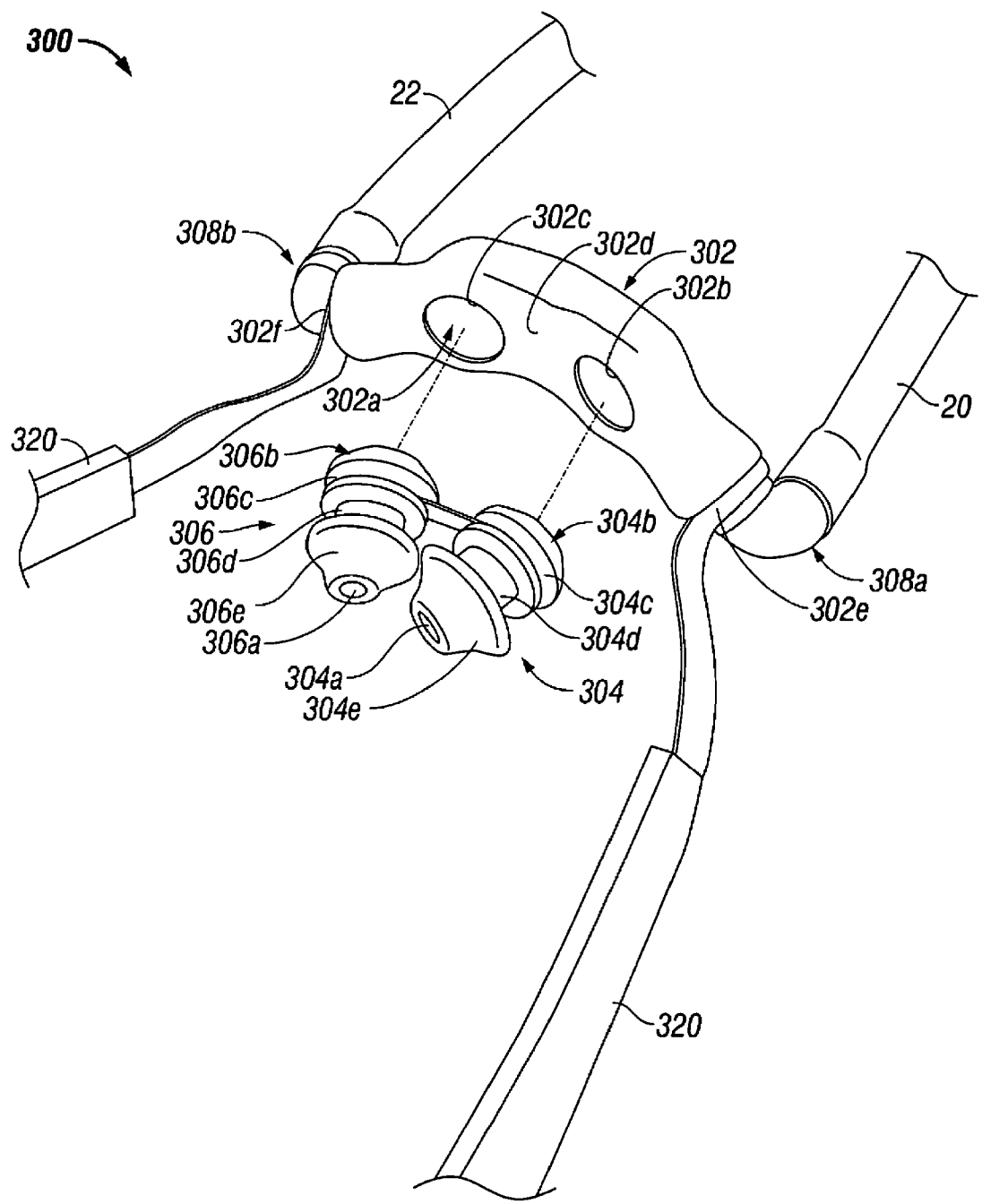
FIG. 10 is a perspective view of the ventilation interface of FIGS. 8 and 9, illustrating a pair of nozzles separated therefrom.

As seen in FIGS. 8 and 10, cannula body 302 includes a pair of apertures 302b, 302c formed therein along a first side 302d thereof. cannula body 302 further includes a pair of opposed apertures 302e, 302f formed therein and configured and adapted to press-fit receive a first end of a respective fluid elbow joint 308a, 308b therein. A second end of each fluid elbow joint 308a, 308b is configured and adapted to press-fit receive an end of respective supply tubes 20, 22. For example, as seen in FIG. 6, the second ends of elbow joints 308a, 308b may include barbs 309 or the like for securely rotatably engaging supply tubes 20, 22. It is envisioned that the first ends of elbow joints 308a, 308b may include barbs (not shown) or the like for securely rotatably engaging to respective opposed apertures 302e, 302f of cannula body 302.

In accordance with the present disclosure, each elbow 308a, 308b is free to rotate about an axis "X" extending through the first end thereof, relative to cannula body 302, as indicated by double-headed arrows "A". Additionally, each supply tube 20, 22 is free to rotate about an axis "Y" extending through the second end of a relative elbow joint 308a, 308b, as indicated by double-headed arrows "B".

Elbow joints 308a, 308b may be right angle elbow joints or may be angled ay any suitable or desired angle. It is envisioned that elbow joints 308a, 308b may be flexible, thereby enabling the angle of the elbow joint to vary when in use. Elbow joints 308a, 308b may be fabricated from a substantially rigid, flexible and/or compliant material, known by one having skill in the art.

As seen in FIG. 10, cannula body 302 includes at least one exhaust or exhalation vent 310 formed therein. A pair of exhaust or exhalation vents 310 are shown, however, it is envisioned that any number of exhaust or exhalation vents may be provided. Each vent 310 defines a lumen or passage into cavity 302a of cannula body 302. Each vent 310 is in axial alignment with a respective nozzle 304, 306. In operation, vents 310 function to allow fluid (i.e., expelled air) to escape from cannula body 302 and to allow excess fluid flow from supply tubes 20, 22 to escape from cannula body 302.

Figure 11:
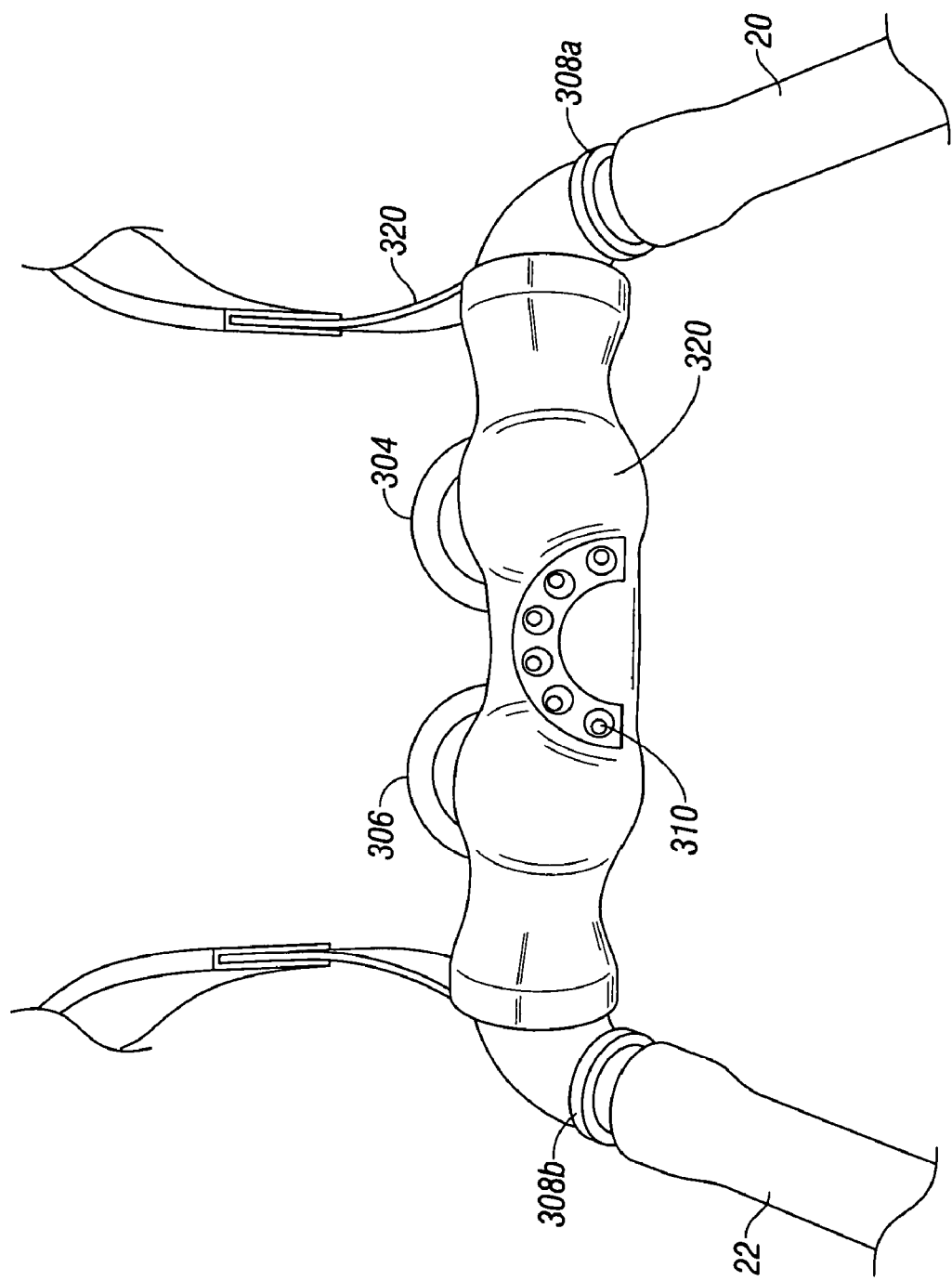
FIG. 11 is a rear perspective view of a cannula body of the ventilation interface of FIGS. 8-10.

As seen in FIG. 11, a plurality of vents 310 may be provided and may be arranged in a semi-circular configuration or the like. Each vent 310 defines a central axis which optionally may be substantially parallel to the central axes extending through nasal pillows 304, 306.

Cannula body 302 may be fabricated from a resilient, elastic material which can be molded and/or formed into a desired shape and which retains its shape and still provides a degree of flexibility, resiliency and/or elasticity, such as, for example, silicone, rubber, polyethylene, polypropylene and the like.

With continued reference to FIGS. 8-11, each nozzle or pillow 304, 306 includes a lumen 304a, 306a extending therethrough for fluid connection with cavity 302a of cannula body 302. Each nozzle 304, 306 includes an enlarged base portion 304b, 306b defining an annular groove 304c, 306c formed therearound, a neck portion 304d, 306d extending from respective base portions 304b, 306b, and a frustoconical or tapered head portion 304e, 306e supported at the end of the respective neck portion 304d, 306d. Nozzles 304, 306 are press-fit into respective apertures 302b, 302c such that annular groove 304c, 306c of nozzles 304, 306 receive edges of apertures 302b, 302c therein.

Each nozzle 304, 306 is fabricated from a resilient, elastic material which can be molded and/or formed into a desired shape and which retains its shape and still provides a degree of flexibility, resiliency and/or elasticity, such as, for example, silicone, rubber, polyethylene, polypropylene and the like.

By providing nozzles 304, 306 which are separable from cannula body 302, nozzles 304, 306 may be replaced as needed and/or desired without having to replace cannula body 302. More over, different sized nozzles 304, 306 may be provided to accommodate differently sized nares of different patients. It is envisioned that a kit including a cannula body 302 and sets of nozzles 304, 306 each having various dimensions and or configurations may be provided. Accordingly, in use, depending on the physical characteristics and/or features of the patient, the doctor or nurse may select appropriately sized and configured nozzles 304, 306 to best accommodate the physical characteristics and/or features of the patient.

Head portion 304e, 306e of each nozzle 304, 306 is free to tilt, flex, bend and/or deflect about neck portion 304d, 306d. Head portion 304e, 306e of each nozzle 304, 306 is free to so move in a complete 360° radius about a longitudinal axis of each nozzle 304, 306. Lumens 304a, 306a extend completely through respective head portions 304e, 306e, respective neck portions 304d, 306d, and respective base portions 304b, 306b Nozzles 304, 306 may be connected to one another via a tether 330 or the like. In use, tether 330 may be divided, i.e., cut, in order to separate nozzles 304, 306 from one another. In this manner, nozzles of varying dimensions may be used in combination with one another in ventilation interface 300 in order to account for our accommodate varying physical characteristics of the patient.

Reference may be made to U.S. Patent Application Publication No. 2006/0124131, filed Jul. 6, 2006, the entire content of which is incorporated herein by reference, for a detailed discussion of the construction and operation of nozzles 304, 306.

As seen in FIGS. 8-17, ventilation interface 300 further includes a strap, head gear or the like 320 for securing cannula body 302 to the head of a patient or the like.

Figure 12:
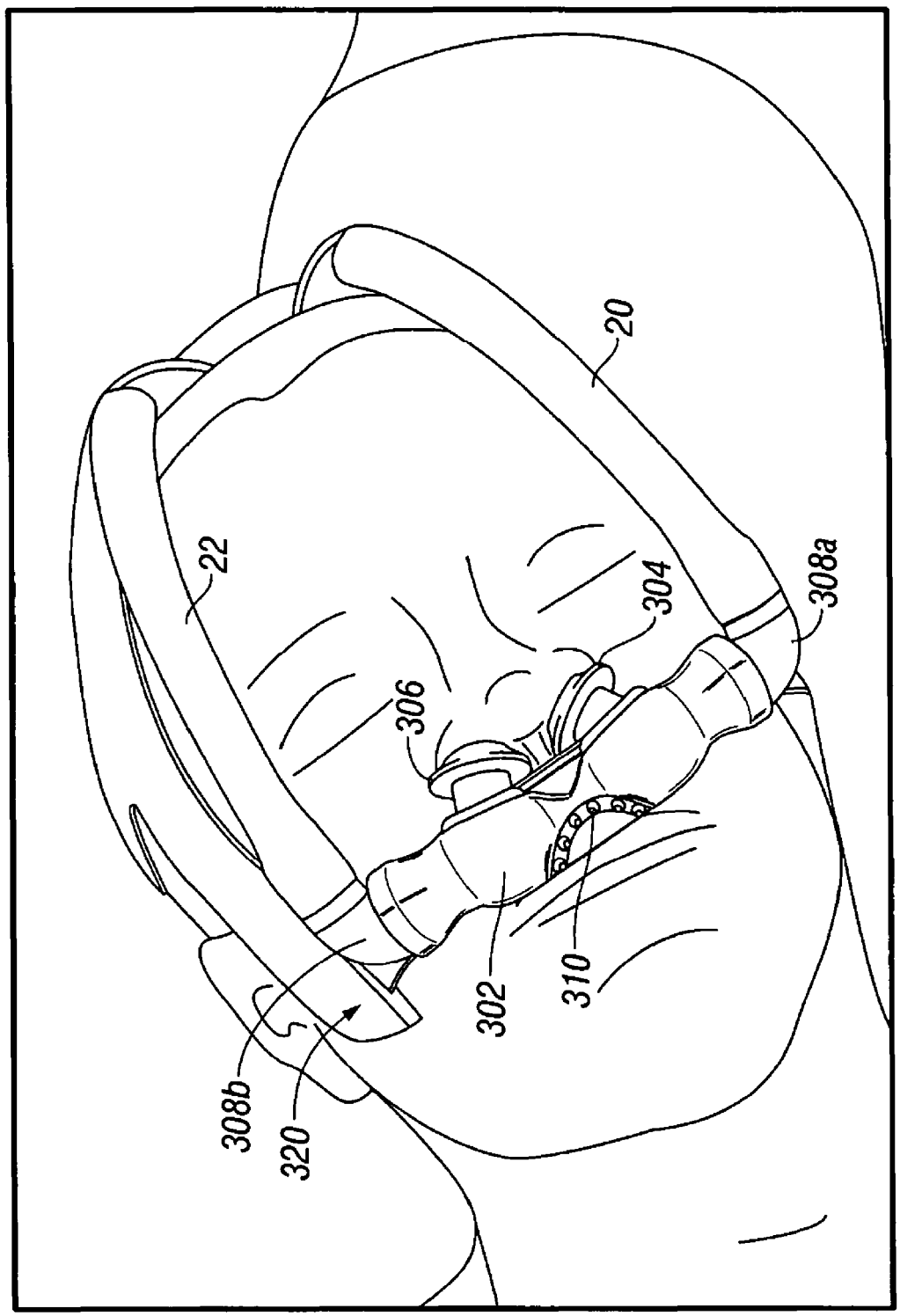
FIG. 12 is a perspective illustration of the ventilation interface of FIGS. 8-11 being worn upon the head of a patient while in a first configuration, wherein the Y-connector located behind the head of the patient.
Figure 13:
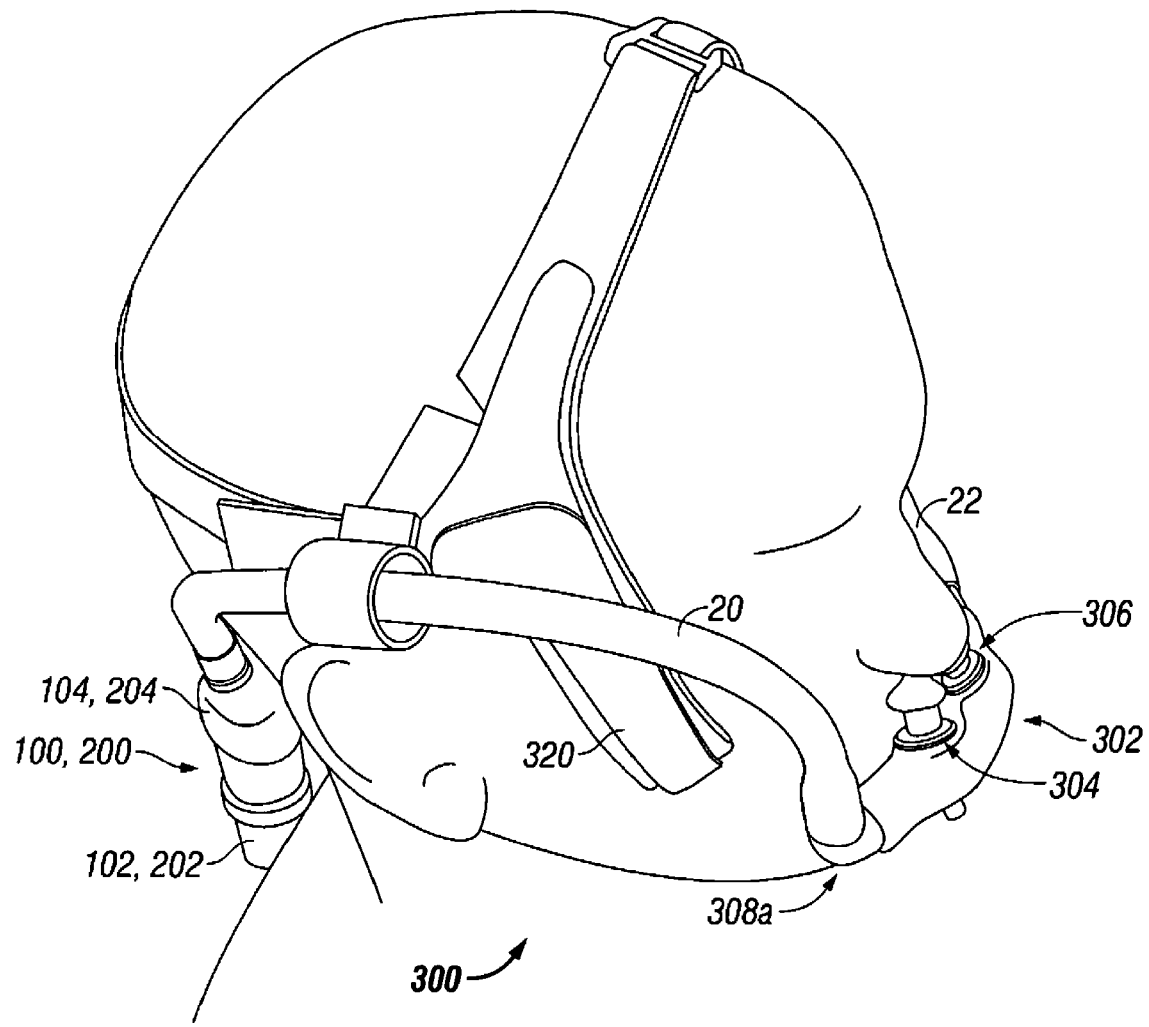
FIG. 13 is a further perspective illustration of the ventilation interface of FIGS. 8-11 being worn upon the head of a patient while in the first configuration, wherein the Y-connector located behind the head of the patient.
Figure 14:
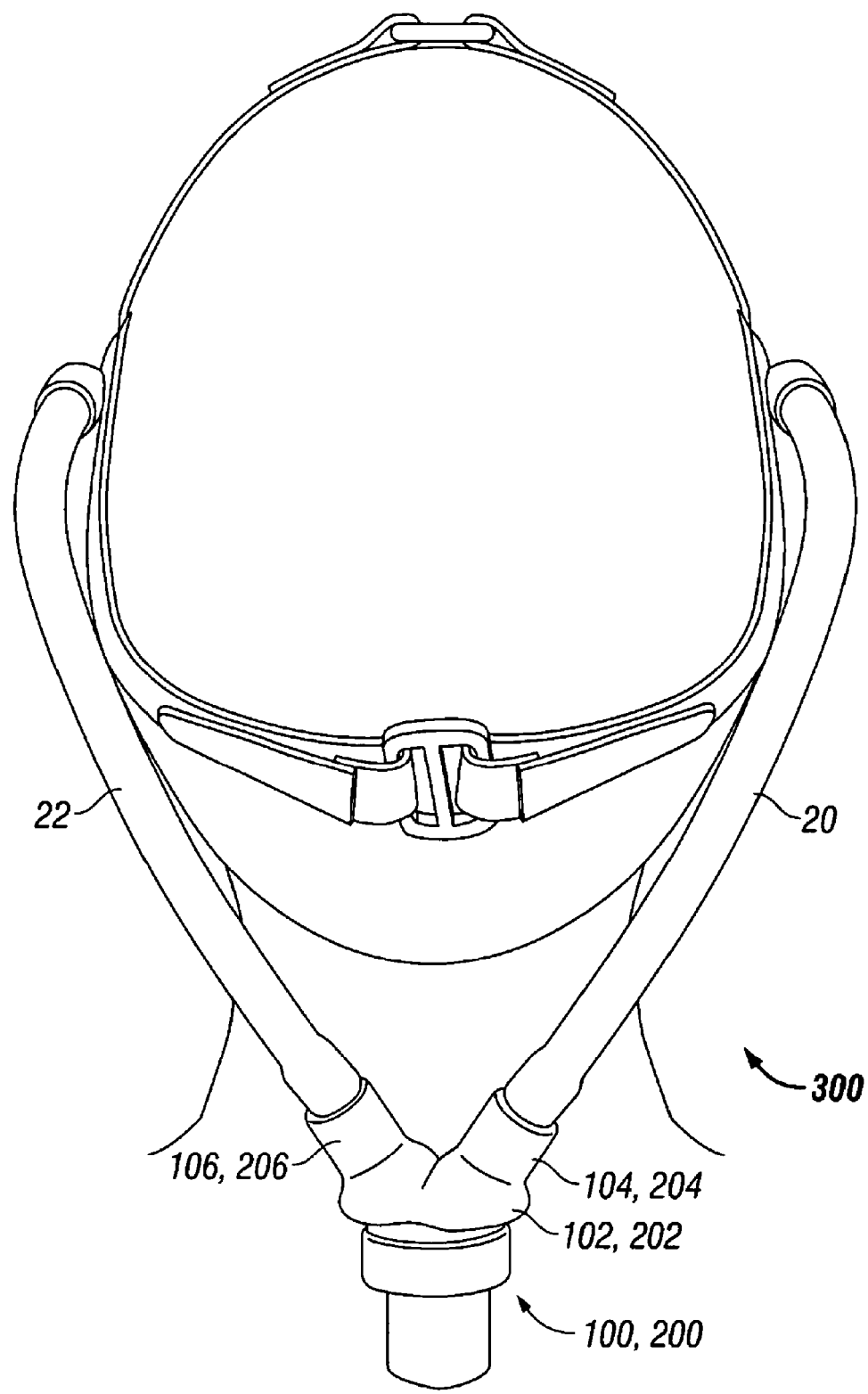
FIG. 14 is still a further perspective illustration of the ventilation interface of FIGS. 8-11 being worn upon the head of a patient while in the first configuration, wherein the Y-connector located behind the head of the patient.

As seen in FIGS. 12-14, ventilation interface 300 may be configured to position Y-connector 100, 100' 200 behind the head of the patient such that supply tubes 20, 22 are positioned on either side of the head of the patient. In this configuration, elbow joints 308a, 308b of ventilation interface 300 are configured such that supply tubes 20, 22 extend over the cheeks of the patient and along the outer side edges of the eyes of the patient. In this manner, the patient may lay the side of their head down on a surface, e.g., a pillow. Additionally, this configuration may be used when the patient is in an upright position (i.e., standing or seated).

Figure 15:
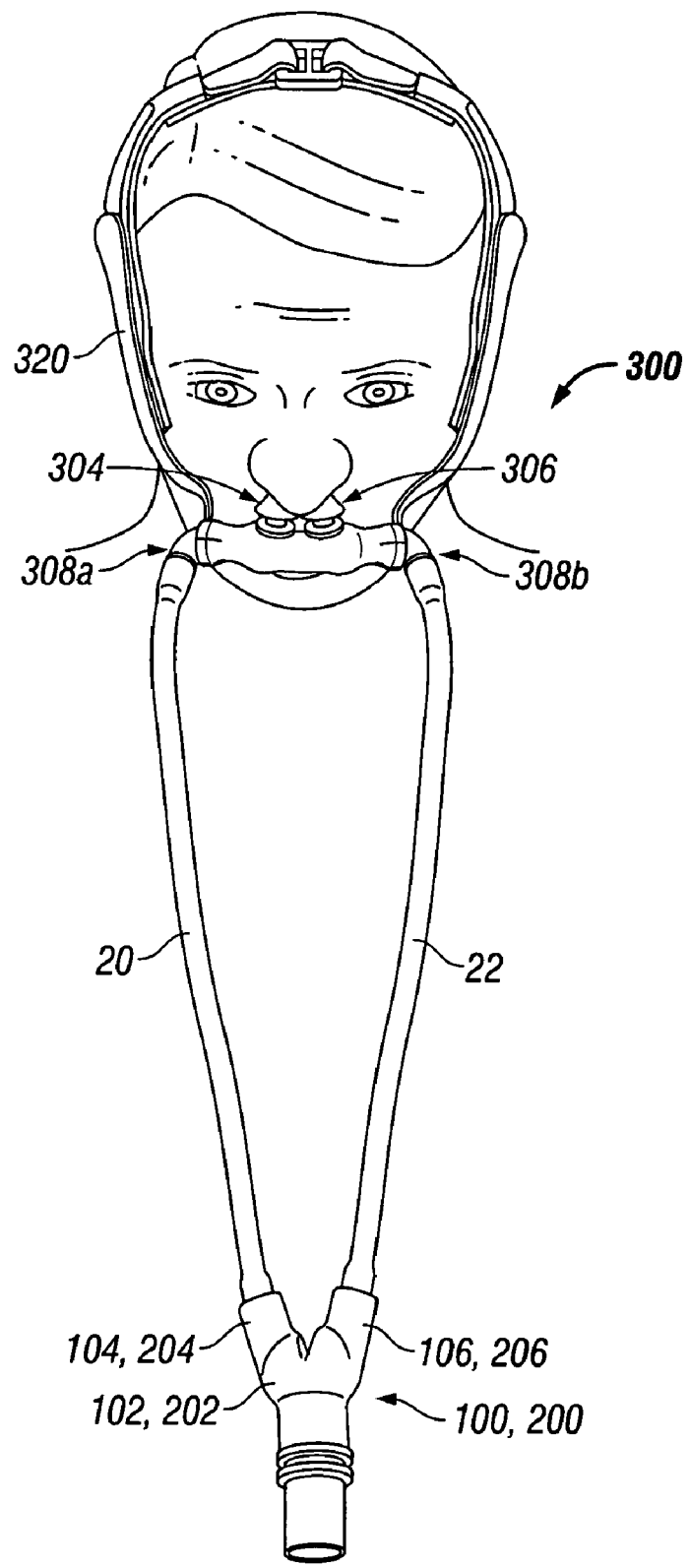
FIG. 15 is a perspective illustration of the ventilation interface of FIGS. 8-11 being worn upon the head of a patient while in a second configuration, wherein the Y-connector located in front of the head of the patient.
Figure 16:
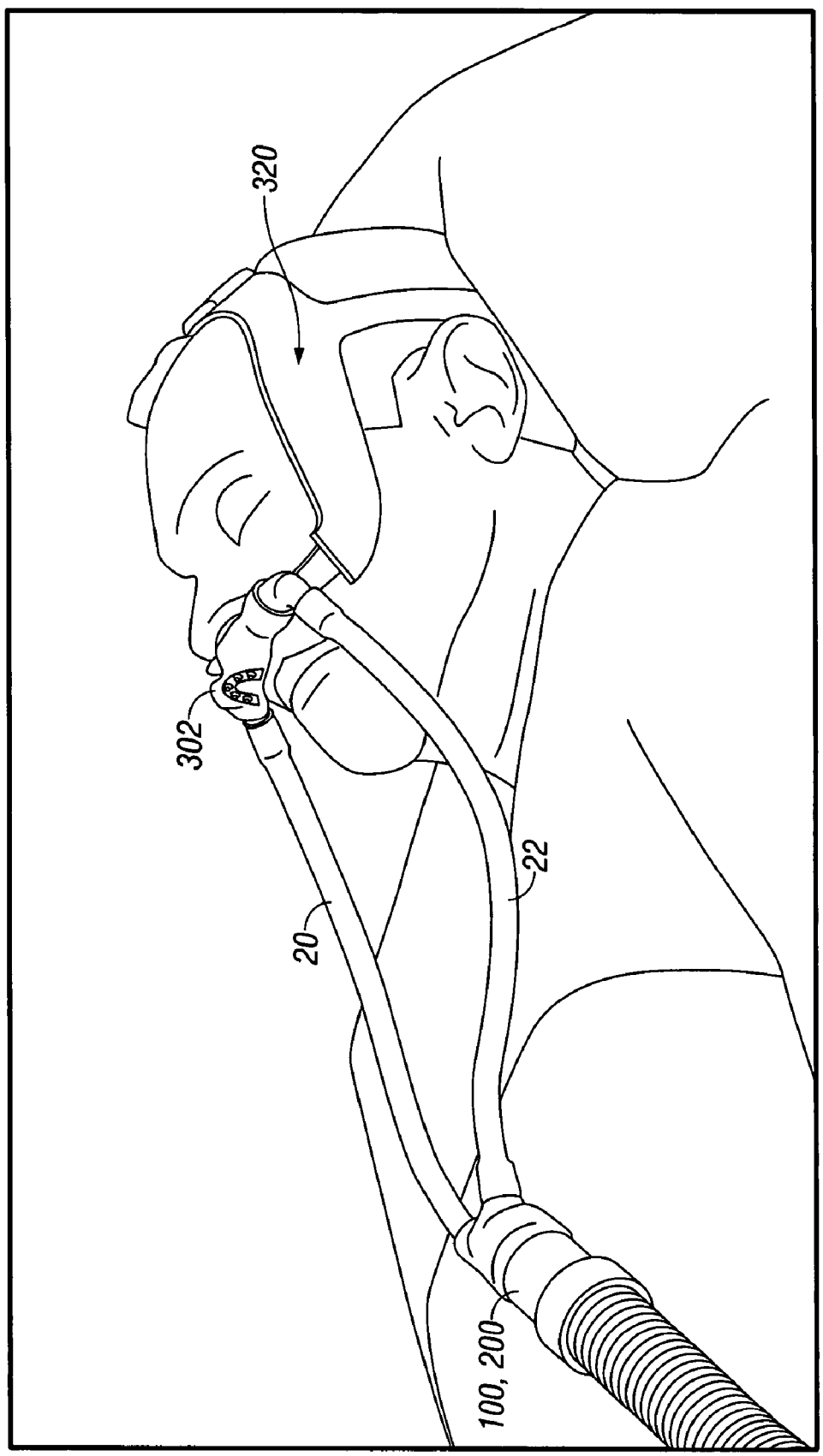
FIG. 16 is a further perspective illustration of the ventilation interface of FIGS. 8-11 being worn upon the head of a patient while in the second configuration, wherein the Y-connector located in front of the head of the patient.

As seen in FIGS. 15 and 16, elbow joints 308a, 308b of ventilation interface 300 may be configured to position Y-connector 100, 100', 200 in front of the head of the patient such that supply tubes 20, 22 are positioned in front of the patient (e.g., on the patients chest or the like). This configuration may be used when the patient is in a recumbent or lying down position.

Figure 17:
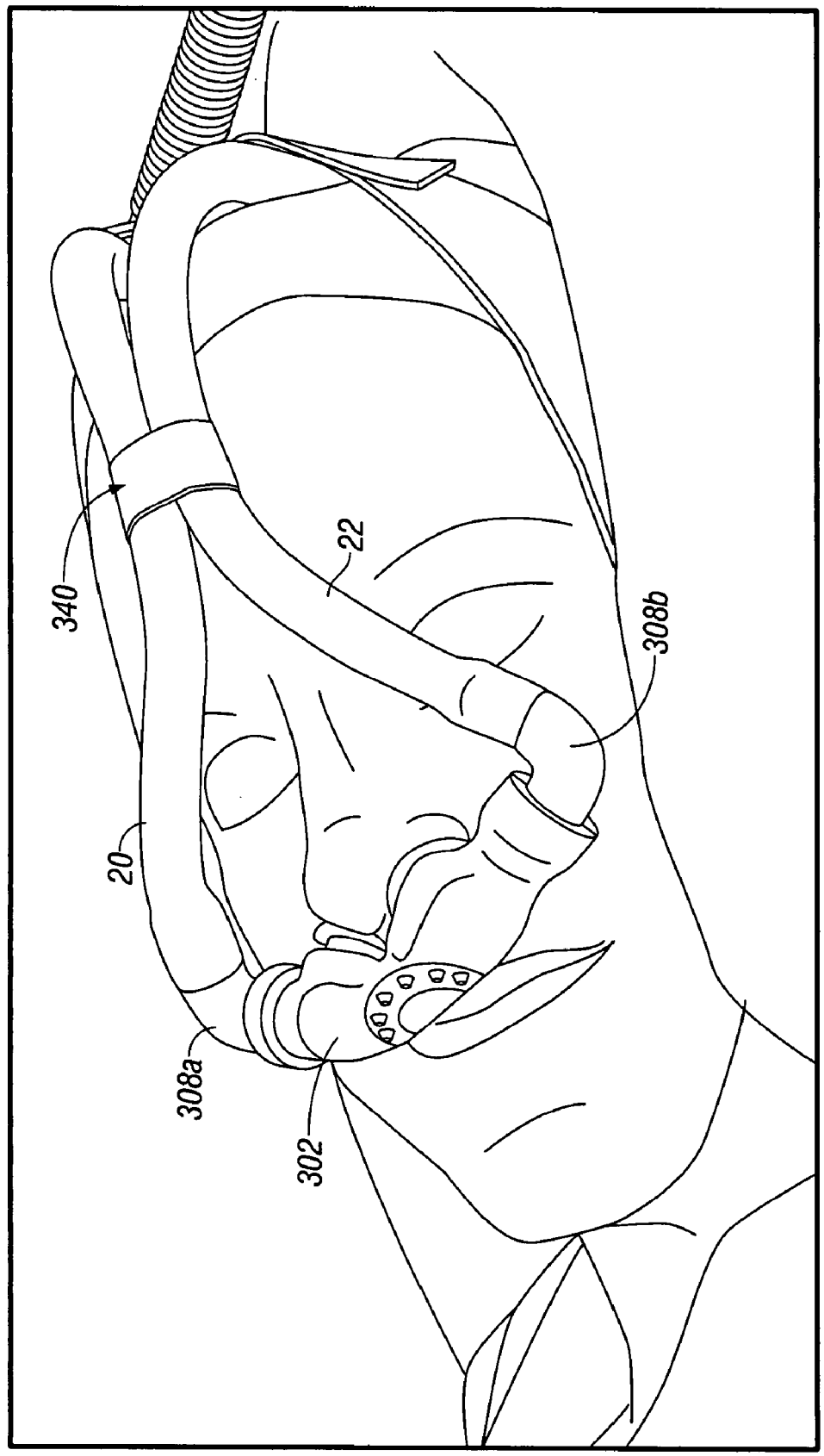
FIG. 17 is a perspective illustration of the ventilation interface of FIGS. 8-11 being worn upon the head of a patient while in a third configuration, wherein the Y-connector located behind the head of the patient and the supply tubes thereof are coupled to one another.

As seen in FIG. 17, ventilation interface 300 may be configured to position Y-connector 100, 100' 200 behind the head of the patient and supply tubes 20, 22 joined to one another using a suitable band 340, such that supply tubes 20, 22 are positioned above the head of the patient. In this configuration, elbow joints 308a, 308b of ventilation interface 300 are configured such that supply tubes 20, 22 extend over the brow of the patient and at least partially over the eyes of the patient. In this manner, the patient may lay the side of their head down on a surface, e.g., a pillow. This configuration may also be used when the patient is in an upright position (i.e., standing or seated).

It is understood that the pivotability and/or movability of body portion, first branch 104, and second branch 106 of Y-connectors 100, 100' and 200, together with the pivotability of elbow joints 308a, 308b of ventilation interface 200, as described above, enables Y-connectors 100, 100' and 200 and ventilation interface 300 to be configured in numerous convenient and comfortable positions such as, for example, the configurations shown in FIGS. 12-17.

The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A connector for interconnecting a conduit of a fluid pressure device to an interface configured to deliver a fluid of the fluid pressure device to a patient, the connector comprising:
a body portion configured for fluid connection to the conduit of the fluid pressure device; and
a first branch and a second branch each extending from and fluidly connected to the body portion, each branch being configured for fluid connection to the interface;
wherein at least one concavity is formed in at least one of the body portion, the first branch and the second branch; and,
wherein the at least one concavity is a thin-walled region.

2. The connector according to claim 1, wherein at least one of the first branch and the second branch is pivotable with respect to the body portion.

3. The connector according to claim 1, wherein the connector is fabricated from a resilient, elastomeric material.

4. The connector according to claim 1, wherein each of the body portion, the first branch and the second branch has a substantially circular transverse cross-sectional profile, and wherein each of the body portion, the first branch and the second branch defines a longitudinal axis.

5. The connector according to claim 1, wherein a longitudinal axis of each of the first and second branches is angled with respect to at least one of each other and with respect to a longitudinal axis of the body portion.

6. The connector according to claim 4, wherein an angle between the longitudinal axes of each of the first and second branches is variable.

7. The connector according to claim 6, wherein the connector is fabricated from a resilient, elastomeric material.

8. The connector according to claim 1, wherein each of the body portion, the first branch and the second branch has a respective wall thickness, and wherein the at least one concavity has a wall thickness which is less than the respective wall thickness.

9. The connector according to claim 1, further comprising a swivel joint connected to the body portion, and a stem extending from the swivel joint.

10. The connector according to claim 1, wherein at least one concavity is a thin-walled region.

11. A respiratory device configured for delivering fluid to a patient from a fluid source, the respiratory device comprising:
a connector for connection to a fluid conduit extending of the fluid source, the connector including:
a body portion configured for fluid connection to the fluid conduit; and
a first branch and a second branch each extending from and fluidly connected to the body portion; wherein at least one of the first branch and the second branch of the connector is pivotable with respect to the body portion thereof; wherein the connector further comprises a swivel joint connected to the body portion, and a stem extending from the swivel joint;
a fluid delivery element extending from each of the first branch and the second branch of the connector; and
a ventilation interface fluidly connected to each of fluid delivery element, the ventilation interface including:
a cannula body defining a cavity;
and at least one engaging element supported on the cannula body and being in fluid communication with the cavity of the cannula body; wherein each fluid delivery element is pivotally connected to the cannula body.

12. The respiratory device according to claim 11, wherein the ventilation interface includes a coupling element configured to pivotally interconnect each fluid delivery element to the cannula body.

13. The respiratory device according to claim 12, wherein each coupling element of the ventilation interface is an elbow.

14. The respiratory device according to claim 12, wherein each coupling element of the ventilation interface is pivotally connected to the cannula body and each fluid delivery element is pivotally connected to a respective coupling element.

15. The respiratory device according to claim 11, wherein each engaging element of the ventilation interface is one of a nozzle and a nasal pillow.

16. The respiratory device according to claim 11, wherein each engaging element is tethered to one another.

17. The respiratory device according to claim 11, wherein the connector is fabricated from a resilient, elastomeric material.

18. The respiratory device according to claim 11, wherein each of the body portion, the first branch and the second branch of the connector has a substantially circular transverse cross-sectional profile, and wherein each of the body portion, the first branch and the second branch of the connector defines a longitudinal axis.

19. The respiratory device according to claim 18, wherein the longitudinal axis of each of the first branch and the second branch of the connector is angled with respect to at least one of each other and with respect to the longitudinal axis of the body portion.

20. The respiratory device according to claim 11, wherein an angle between a longitudinal axis of each of the first branch and the second branch of the connector is variable.

21. The respiratory device according to claim 20, wherein the connector is fabricated from a resilient, elastomeric material.

22. The respiratory device according to claim 11, wherein at least one concavity is formed in at least one of the body portion, the first branch and the second branch; and wherein each of the body portion, the first branch and the second branch of the connector has a respective wall thickness, and wherein the at least one concavity of the connector has a wall thickness which is less that the respective wall thickness.

23. The respiratory device according to claim 11, wherein the connector further comprises a swivel joint connected to the body portion, and a stem extending from the swivel joint.

24. The respiratory device according to claim 11, wherein at least one concavity is formed in at least one of the body portion, the first branch and the second branch, and wherein the at least one concavity of the connector is a thin-walled region.

25. A connector for interconnecting a conduit of a fluid pressure device to an interface configured to deliver a fluid of the fluid pressure device to a patient, the connector comprising:
   a body portion configured for fluid connection to the conduit of the fluid pressure device;
   a first branch and a second branch each extending from and fluidly connected to the body portion, each branch being configured for fluid connection to the interface; and
   a swivel joint connected to the body portion, and a stem extending from the swivel joint;
   wherein at least one concavity is formed in at least one of the body portion, the first branch and the second branch.

26. A connector for interconnecting a conduit of a fluid pressure device to an interface configured to deliver a fluid of the fluid pressure device to a patient, the connector comprising:
   a body portion configured for fluid connection to the conduit of the fluid pressure device; and,
   a first branch and a second branch each extending from and fluidly connected to the body portion, each branch being configured for fluid connection to the interface;
   wherein each of the body portion, the first branch and the second branch defines a longitudinal axis, and
   wherein the longitudinal axis of at least one of the first branch and second branch can be variably angled with respect to at least one of each other and to the longitudinal axis of the body portion.

27. The connector according to claim 26, wherein an angle between the longitudinal axis of the body portion and the longitudinal axis of the at least one of the first branch and second branch can be varied during use.

28. The connector according to claim 26, wherein an angle between the longitudinal axis of the body portion and the longitudinal axis of the at least one of the first branch and second branch can be varied to accommodate for a user wearing position.

* * * * *